United States Patent [19]

Jacks et al.

[11] 3,975,343

[45] Aug. 17, 1976

[54] SOLUBILIZATION OF PROTEIN WITH ETHANOL-ACETONITRIL-WATER SOLVENT SYSTEM

[75] Inventors: Thomas J. Jacks, Metairie, La.; Robert H. Barker, Easley, S.C.; Thomas P. Hensarling, Metairie, La.

[73] Assignee: The United States of America as represented by the Secretary of Agriculture, Washington, D.C.

[22] Filed: June 27, 1975

[21] Appl. No.: 591,251

[52] U.S. Cl. .......................... 260/112 R; 23/230 B; 252/364; 356/36
[51] Int. Cl.² ...................... C07G 7/00; G01N 33/16
[58] Field of Search .............. 23/230 B; 260/112 R; 252/364; 356/36

[56] References Cited
UNITED STATES PATENTS
3,856,471   12/1974   Winitz et al...................... 23/230 B

OTHER PUBLICATIONS

Kaplan, D. M. and Woodward, D. O., Evaluation of . . Mitochodrial Membrane Protein Preparations; Analytical Biochemistry 52, 102–110 (1973).

West et al., Textbook of Biochemistry, 4th ed., 1966, p. 262.

Scheflan et al., The Handbook of Solvents, 1953, pp. 87 and 88.

Visser et al., An Automated Procedure for Circular Dichroism and Optical Rotary Dispersion Spectroscopy; Analytical Biochemistry 60, 59–77 (1974).

Primary Examiner—Norman Yudkoff
Assistant Examiner—Dale Lovercheck
Attorney, Agent, or Firm—M. Howard Silverstein; David G. McConnell; Salvador J. Cangemi

[57] ABSTRACT

A solvent system composed of ethanol-acetonitrile-water dissolved certain membrane proteins of biological origin. The solvent system was optically transparent to ultraviolet radiation from 200 to 400 nanometers (nm). This transparency permitted ascertainment of spectral characteristics of membrane proteins at these wavelengths.

4 Claims, 1 Drawing Figure

Curve 1

Curve 2

Curve 3

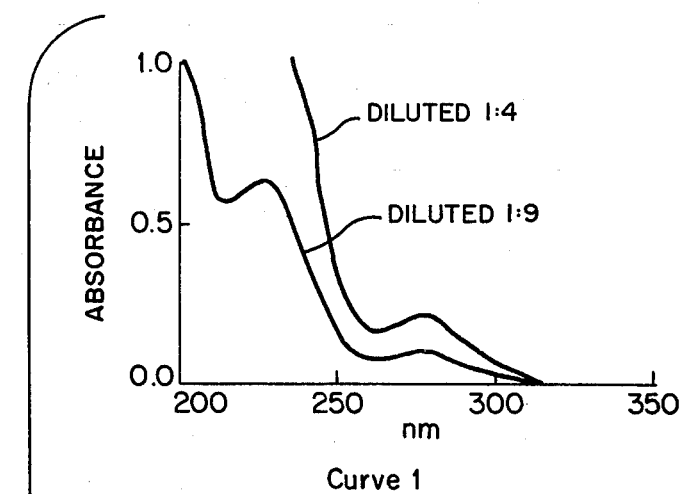
Curve 1
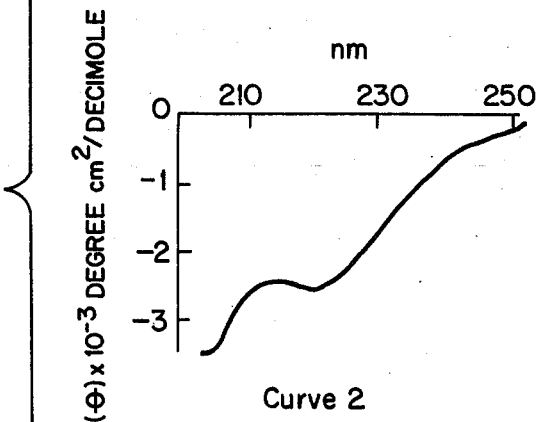
Curve 2
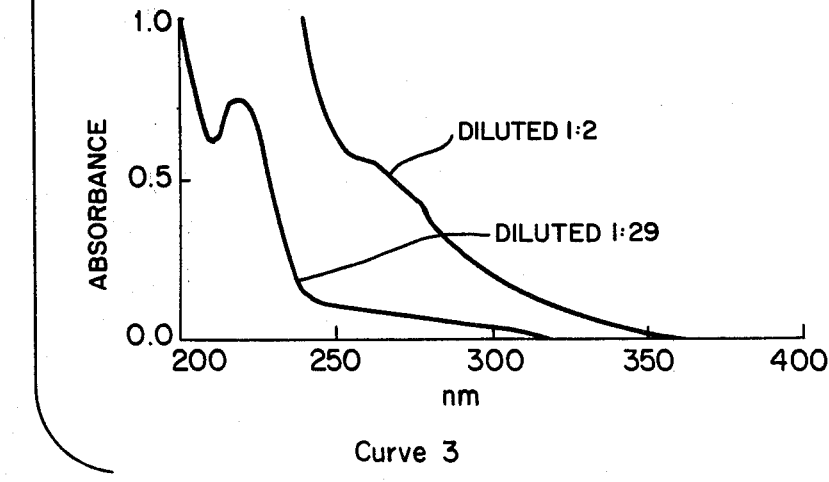
Curve 3

SOLUBILIZATION OF PROTEIN WITH ETHANOL-ACETONITRIL-WATER SOLVENT SYSTEM

This invention relates to a solvent for dissolving proteins of biological origin. Specifically, this invention relates to a solvent for dissolving membrane proteins of biological origin. More specifically, this invention relates to an optically transparent solvent for dissolving membrane proteins of biological origin. Even more specifically, this invention relates to the use of the optically transparent solvent system composed of ethanol-acetonitrile-water (about 4:1:1, v/v) for dissolving certain membrane proteins of biological origin.

As employed in this specification the term optical transparency refers to a physical characteristic of a solvent wherein the solvent does not absorb ultraviolet light, allowing light absorption or spectral characteristics of the solute to be examined. The solute, in this case, is membrane protein; most other proteins are not soluble in this solvent.

The primary object of this invention is to provide a solvent for dissolving membrane proteins of biological origin.

The second object of this invention is to provide a protein solvent that is optically transparent in the ultraviolet energy region of 200 to 400 nm.

BACKGROUND AND PRIOR ART

Membrane proteins of biological tissues are insoluble in water, in salt solutions, or in other media in which most other proteins are soluble. Thus, other solvents have been developed for dissolution of membrane proteins. These solvents include aqueous solutions of detergents, dilute acid, aqueous solutions of protein perturbants such as urea, sodium hydroxide, etc., and aqueous solutions of chloral hydrate. However, these solvents are not optically transparent to ultraviolet radiation throughout the range of 200 to 400 nanometers (nm). Consequently, measurements of spectral properties of membrane proteins could not be obtained at these wavelengths. Such measurements are needed for estimations of protein concentrations from ultraviolet absorbances and of the amounts of secondary structures comprising protein conformations from ultraviolet circular dichroism.

We have now discovered a solvent system that not only dissolves certain membrane proteins but also is optically transparent to ultraviolet and visible radiation from 200 to 400 nm. By the method of the instant invention, a new mixed solvent consisting of about 4 parts ethanol, 1 parts acetonitrile and 1 part water is used to dissolve certain membrane protein. Although all ratios will yield an optically transparent solution not all ratios will dissolve the membrane protein. The absorbance and circular dichroic spectra of the resultant protein solution can then be examined throughout the electromagnetic wavelength range of 200 to 700 nm, but especially at ultraviolet radiation from 200 to 400 nm.

DESCRIPTION OF THE DRAWING

The single FIGURE in the drawing shows curves illustrating properties of the solution.

EVALUATIONS OF SOLVENT SYSTEM OF THE PRESENT INVENTION

Ultraviolet spectra of protein solutions from 200 to 400 nm were obtained with a Beckman model DK-2 recording spectrophotometer. Amount of protein dissolved in ethanol-acetonitrile-water was determined from the ratio of absorbances of the solution at 260 nm and 280 nm (ref. J. M. Clark, Jr., "Experimental Biochemistry," W. H. Freeman, Co., San Francisco, 1964, p. 76).

Circular dichroic spectra of protein solutions from 200 to 400 nm were obtained with a Cary model 60 recording spectropolarimeter equipped with a 6001 CD attachment. Calculations of the secondary structure of the protein from the circular dichroic spectrum were performed as described by T. J. Jacks et al., International Journal of Peptide and Protein Res. 5: 289–291, 1973.

EXAMPLE 1

Lipid-rich spherosomes were isolated from peanut seeds as described previously by T. J. Jacks et al., Plant Physiol. 42:585-597, 1967, and defatted by extraction with 13 volumes of acetone-hexane (10:3, v/v) at 0° Celsius. The membrane residue was further defatted sequentially with 2.5 volumes of ice-cold hexane-acetone (3:2, v/v) two extractions with 2 volumes of ice-cold acetone, and three extractions with 0.2 volumes of diethyl ether. After being dried in vacuo, the resultant membrane, which is about 70% protein, was dissolved in ethanol-acetonitrile-water (4:1:1, v/v) at a concentration of 1.4 mg of membrane per ml of solvent. The ultraviolet absorbance spectrum of the appropriately diluted solution of membrane protein was determined spectrophotometrically and is plotted in Curve 1. Calculations from the 260 nm and 280 nm portions of the spectrum indicated that the original, undiluted solution contained 0.98 mg of protein per ml.

The isolation and preparation was repeated to make other investigative studies. The circular dichroic spectrum of the solution of membrane protein was determined spectropolarimetrically and is plotted in Curve 2. Calculations from the spectrum indicate that the membrane protein consists of 0.0% alpha-helical, 30.7% pleated sheet, and 69.3% unordered structures.

($\theta$) × $10^{-3}$ degree cm$^2$/decimole

EXAMPLE 2

Mitochondria of peanut seedlings were isolated, defatted, and dehydrated as described previously by L. Y. Yatsu and T. L. Jacks, Plant Physiol. 49:937–943, 1972. After being dried, the membrane, which is about 43% protein, was dissolved in ethanol-acetonitrile-water at a concentration of 1.4 mg of membrane per ml of solvent. The absorbance spectrum of the appropriately diluted solution was determined spectrophotometrically and is shown in Curve 3. Calculations from the 260 nm and 280 nm portions of the spectrum indicated that the original, undiluted solution contained 0.60 mg of protein per ml.

OBSERVATIONS

The analyses determined from Curves 1–3 were unattainable without the use of the ethanol-acetonitrile-water solvent.

We claim:

1. A process for dissolving membrane proteins of biological origin comprising mixing about 1.4 mg of membrane with 1 ml of a solvent mixture which is made up of about 4 parts ethanol, 1 part acetonitrile, and 1 part water, and which is transparent to ultraviolet and visible radiation in the spectrum of about from 200 to 400 namometers.

2. A process for dissolving membrane protein of biological origin comprising mixing about 1.4 mg of the membrane selected from the group consisting of spherosomal membranes and mitochondrial membranes with 1 milliliter of a solvent mixture, which is transparent to ultraviolet and visible radiation in the spectrum of about from 200 to 400 nanometers, and consisting of ethanol-acetonitrile-water in a volume to volume ratio respectively of about 4:1:1; and stirring thoroughly until homogeneity is attained, as manifested by its transparency.

3. The process of claim 2 wherein the membrane is spherosomal.

4. The process of claim 2 wherein the membrane is mitochondrial.

* * * * *

UNITED STATES PATENT OFFICE
CERTIFICATE OF CORRECTION

Patent No. 3,975,343                     Dated August 17, 1976

Inventor(s) Thomas J. Jacks, Robert H. Barker, Thomas P. Hensarling, Lawrence Y. Yatsu, and Navin J. Neucere It is certified that error appears in the above-identified patent and that said Letters Patent are hereby corrected as shown below:

[75] Inventors: Thomas J. Jacks, Metairie, La.; Robert H. Barker, Easley, S. C., Thomas P. Hensarling, Metairie, La.; Lawrence Y. Yatsu, New Orleans, La.; and Navin J. Neucere, New Orleans, La.

Signed and Sealed this

Fourth Day of January 1977

[SEAL]

Attest:

RUTH C. MASON
Attesting Officer

C. MARSHALL DANN
Commissioner of Patents and Trademarks